(12) United States Patent
Aaslyng et al.

(10) Patent No.: US 6,379,653 B1
(45) Date of Patent: Apr. 30, 2002

(54) TOOTH BLEACHING

(75) Inventors: Dorrit Aaslyng, Værløse; Rie Tsuchiya, Birkerod, both of (DK); Abdul Gaffar, Princeton; Sahar F. Smith, Bordenton, both of NJ (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/384,921

(22) Filed: Aug. 27, 1999

Related U.S. Application Data

(63) Continuation of application No. 09/019,261, filed on Feb. 5, 1998, now Pat. No. 5,989,526, and a continuation of application No. PCT/DK96/00350, filed on Aug. 19, 1996.

(30) Foreign Application Priority Data

Aug. 18, 1995 (DK) ............................................. 0926/95
Sep. 20, 1995 (DK) ............................................. 1048/95

(51) Int. Cl.[7] ........................... A61K 7/16; A61K 7/28; A61K 7/30
(52) U.S. Cl. .......................................... 424/50; 424/49
(58) Field of Search ..................... 424/49–58

(56) References Cited

U.S. PATENT DOCUMENTS

| | | | | |
|---|---|---|---|---|
| 4,150,113 A | * | 4/1979 | Hoogendoorn et al. | 424/50 |
| 4,178,362 A | * | 12/1979 | Hoogendoorn et al. | 424/50 |
| 4,537,764 A | * | 8/1985 | Pellico et al. | 424/50 |
| 4,578,265 A | * | 3/1986 | Pellico et al. | 424/50 |
| 5,270,194 A | * | 12/1993 | D'Alterio et al. | 435/188 |
| 5,362,512 A | * | 11/1994 | Cabrera et al. | 426/601 |
| 5,578,336 A | * | 11/1996 | Monte | 426/72 |
| 5,698,245 A | * | 12/1997 | Tanaka et al. | 426/10 |
| 5,741,688 A | * | 4/1998 | Oxenboll et al. | 435/190 |
| 5,747,078 A | * | 5/1998 | De Jong et al. | 426/9 |
| 5,834,280 A | * | 11/1998 | Oxenboll et al. | 435/190 |
| 5,866,406 A | * | 2/1999 | Wagner et al. | 435/190 |
| 5,989,526 A | * | 11/1999 | Aaslyng et al. | 424/50 |

FOREIGN PATENT DOCUMENTS

JP     63 309269     6/1987

* cited by examiner

*Primary Examiner*—Shep K. Rose
(74) *Attorney, Agent, or Firm*—Elias Lambiris

(57) ABSTRACT

The present invention provides safe products for bleaching teeth. Oral compositions comprising at least one oxidoreductase fulfil criteria without the presence of peroxide or with only very little peroxide present. The invention also relates to an oral care product comprising the oral composition of the invention, a method of bleaching teeth, a method for using said oral care products and the use of oxidoreductases for oxidation of teeth stains.

6 Claims, No Drawings

TOOTH BLEACHING

CROSS-REFERENCE TO RELATED APPLICATIONS

This application is a continuation of U.S. application Ser. No. 09/019,261 filed Feb. 5, 1998 now U.S. Pat. No. 5,989,526 which claims priority under 35 U.S.C. 119 Danish application Ser. Nos. 0926/95 filed Aug. 18, 1995 and 1048/95 filed on Sep. 20, 1995 and priority under 35 U.S.C. 120 of application Ser. No. PCT/DK96/00350 filed Aug. 19, 1996 in the PCT, the contents of which are fully incorporated herein by reference.

FIELD OF THE INVENTION

The present invention relates to an oral composition for bleaching teeth without the presence of peroxide or comprising only very little peroxide, an oral care product comprising the oral composition of the invention, a method of bleaching teeth, a method for using said oral care product and the use of oxidoreductases for oxidation of teeth stains.

BACKGROUND OF THE INVENTION

Most people want to have a mouth full of dazzling white teeth, as the teeth constitute an important part of the overall picture of the human face especially when smiling. In contrast hereto strongly discoloured teeth entail an unhealthy and in certain cases even repellent "look".

For many years, crowns or dentures were seen as the only means for avoiding e.g. the yellowing of teeth coming with age, discolouration of teeth due to long term intake of the antibiotic tetracycline during childhood, or the yellowish brown to black discolouration of teeth as a consequence of coffee drinking, tobacco smoking/chewing etc.

Even though techniques for bleaching teeth have been known for many years, tooth bleaching has never been used extensively, until recently.

The first published tooth bleaching technique used oxalic acid as the bleaching agent and was reported by Chaple in the 1877. Soon after, the first report of peroxide used as a bleaching agent was published by Harlan in 1884. Even though quite a number of bleaching agents have been suggested since then peroxide is today still the most commonly used agent.

The structure of teeth

A mammal tooth is chiefly composed of four main constituents namely the "cementum", the "dental pulp", the "dentin", and the "enamel".

The "cementum" is bonelike tissue forming the outer surface of the root of the tooth. The "dental pulp" consists of sensitive tissue containing arteries, veins, and lymphatic and nerve tissue. The "dentin" which surrounds the dental pulp forms the major part of the tooth. The dentin is dense bonelike calcareous tissue. On the outside of the tooth there is a hard porous layer composed of hydroxyapatite mineral crystals having a natural opaque white or off-white colour. This outer porous layer is called the "enamel".

Tooth discolouration

Tooth discolouration can be caused by a variety of intrinsic and/or extrinsic influences. In general stains are divided into two main categories: 1) extrinsic stains and 2) intrinsic strains.

1) Extrinsic stains

Extrinsic stains are mainly caused by the daily intake of substances, such as foods and beverages through the mouth, and/or the use of tobacco products etc. These substances tend to adhere to the enamel's hydoxyapatite structure and hereby discolour the teeth and/or reduce the whiteness of the teeth.

Over a period of years extrinsic stains may penetrate the enamel layer and gradually give intrinsic discolourations.

2) Intrinsic stains

Intrinsic stains are the term used for stains which have penetrated the tooth structure (i.e. discolouration within the tooth matrix). Such stains can arise as described above or be caused by agents including haematological agents and certain drugs, or be due to dental pulp necrosis or developmental abnormalities.

For instance, degradation products from the body may cause discolorations. Excessive intake of tetracycline or fluoride during a long period of illness has been found to release degradation products into the dentinal tubules during the development of tooth enamel causing some degree of discolouration. The severity of such discolouration depends on the time and duration of intake of the medicine.

Further, dental pulp necrosis entails Haemorrhagic discolorations and is a result of blood degradation. If the pulp necrosis is caused by e.g. caries degradation of proteins the tooth/teeth will become greyish-brown.

In the case of traumatic pulp death the tooth will turn yellow-brown. It is believed that such a discolouration is caused by haemolysis of red blood cells entering the dentinal tubules.

Tooth bleaching

Before conducting tooth bleaching it is important to assess the type of stain, as different types of stains need different approaches and/or bleaching agents.

Certain extrinsic stains, which occur on the surface or subsurface of the teeth, can be removed by regular intense mechanical brushing of the teeth with cleansing agents containing abrasives and surfactants. However, not all extrinsic stains can be removed this way and require bleaching agents which inhibit non-enzymatic browning reactions.

Intrinsic stains are located in the tooth matrix and cannot be removed or prevented by intense mechanical brushing of the teeth. Removal of such discolourations requires bleaching agents capable of penetrating into the teeth structure. Hydrogen peroxide is an example of such an agent, which can be used for both extrinsic and intrinsic stains.

Hydrogen peroxide can be used for many types of stains e.g. stains residing in the dentin, such as stains caused by tetracycline.

Even though hydrochloric acid is not regarded as being a bleaching agent it is known to be capable of removing stains caused by fluorosis, as it dissolves the surface of the teeth.

However, the use of such agents can inflict severe tooth damage or at least irritation in the oral cavity. Consequently, such agents are for safety reasons not suitable for "home-use" by the private consumer and should only be used precautiously by professionals.

Bleaching techniques

Bleaching techniques are usually divided into two main categories:

a) non-vital bleaching techniques, and b) vital bleaching techniques.

a) Non-vital bleaching

The non-vital techniques give the most effective results but also have the greatest potential hazard. One non-vital bleaching technique uses sodium perborate and 35% hydrogen peroxide as the active ingredient.

b) Vital bleaching

Products sold for vital bleaching techniques can be divided into three main groups a) "in-office" bleaching products, b) dentist prescribed, home applied bleaching products, and c) over-the-counter bleaching kits.

For further information concerning the categorisation of tooth bleaching products and techniques we refer to Van B. Haywood, (1992), Periodontology and Restorative Dentistry, p. 142–149.

One of the most commonly used "in-office"-techniques combines the use 30% hydrogen peroxide with heat and light treatment to speed up the oxidation reaction (i.e. the removal of stains).

Another method, using a "dentist prescribed, home-applied"-bleaching product, involves the use of 10% urea peroxide (carbamide peroxide). The teeth are bleached in a mouth tray, containing the bleaching agent, placed upon the teeth of the patient.

Over-the-counter kits which can be used for bleaching teeth include products such as toothpastes and mouth washes having from 3% to 6% hydrogen peroxide and are sold directly to the consumer, without prescription by a dentist. Comments to prior art Most of the above mentioned prior art methods/techniques involve the use of peroxides and/or other agents in concentrations which are not safe for "home-use" by the private consumer due to the risk of damaging the teeth and/or the oral tissue.

Furthermore, effective concentrations of e.g. hydrogen peroxide exceed the allowed limits in certain countries.

Products comprising low concentration of bleaching agents, such as hydrogen peroxide, are considered to have slow bleaching effect.

Therefore, there is a need for providing safe tooth bleaching compositions, which do not comprise harmful concentrations of peroxide and/or other hazardous agents. It is further desirable that such tooth bleaching compositions can be used as components in conventional oral care products for "home-use" by the private consumer.

SUMMARY OF THE INVENTION

The object of the present invention is to provide safe tooth bleaching products, which do only comprise very low concentrations of peroxides or/and other hazardous bleaching agents.

The present inventors have surprisingly found that tooth bleaching compositions comprising at least one oxidoreductase have a good bleaching effect without causing the problems that high concentrations of peroxides and other agents may cause.

Consequently, in the first aspect the object of the present invention is to provide an oral composition for bleaching teeth comprising at least one oxidoreductase, such as a laccase or a related enzyme, and/or an oxidase and/or a peroxidase.

In the second aspect the invention relates to an oral care product, comprising an oral composition for bleaching teeth of the invention.

The invention also relates to a method for bleaching discoloured or stained teeth, and a method for using an oral composition or an oral care product in the oral cavity.

Finally the invention relates to the use of oxidoreductases for vital and non-vital bleaching of teeth.

DETAILED DESCRIPTION OF THE INVENTION

The object of the present invention is to provide safe tooth bleaching products which do only comprise very low concentrations of peroxides or/and other hazardous agents.

In an embodiment of the invention it is even possible to omit peroxide and/or other equivalent agents completely from the composition.

In the context of the present invention the term "bleaching" of teeth is equivalent with the terms "whitening" or "brightening" of teeth.

The term "low concentrations" of e.g. peroxide means concentration of from 0% (no peroxide present) to about 1% peroxide, calculated on the basis of the weight of final oral composition or oral care product.

All concentrations mentioned in the connection with the present invention are calculated in weight per cent.

Safe oral compositions and oral care products of the invention may comprise from 0% to 0.5% peroxide, such as less than about 0.3%, which may be about 0.1% peroxide. Preferably the concentration of peroxide lies from 0% to 1%.

It is to be understood that even though less than 1% of peroxide is needed for obtaining a tooth bleaching effect of the 9invention, it is contemplated to add concentration of peroxide that is higher than 1%, such as 3% or 6% and even 10% calculated on the basis of the weight of the final oral composition or oral care product.

However, if peroxide is present in higher concentrations it may damage the oral tissue. Further, the stain oxidising enzyme may be inactivated at such concentrations.

The use of oral care product comprising an oral composition of the invention facilitates the bleaching of teeth. For instance oral care products of the invention in the form of a toothpaste or a mouth wash make it possible to incorporate tooth bleaching as a natural part of the daily teeth cleaning and/or mouth rinsing at home.

The present inventors have surprisingly found that safe tooth bleaching compositions can be provided by adding an enzyme or enzyme system capable of oxidising the teeth stains.

In the first aspect the invention relates to an oral composition for bleaching teeth comprising at least one enzyme within the group of oxidoreductases as the active bleaching ingredient(s).

Oxidoreductases (i.e. enzymes classified under the Enzyme Classification number E.C. 1 (Oxidoreductases) in accordance with the Recommendations (1992) of the International Union of Biochemistry and Molecular Biology (IUBMB)) which are enzymes catalysing oxidoreductions.

Within the group of oxidoreductases enzymes are preferred which catalyse the oxidation of a substrate (an electron or hydrogen donor) by acting on oxygen ($O_2$) and/or a peroxide as the acceptor. Such enzymes include enzymes classified within the enzyme classes comprising oxidases including E.C. 1.1.3. E.C. 1.2.3, E.C. 1.3.3, E.C. 1.4.3, E.C. 1.5.3, E.C. 1.7.3, E.C. 1.8.3, E.C. 1.9.3, laccases and related enzymes comprised in E.C. 1.10.3 and peroxidases in E.C. 1.11.

In the case of an enzyme acting on oxygen ($O_2$) as the acceptor, said oxygen may be molecular oxygen supplied by the air.

If a peroxide, for instance $H_2O_2$ or $H_2O_2$-generation compounds such as perborat and percarbonate, is added to the oral composition or oral care product it will be added in the above mentioned concentrations.

Enzymes' or enzyme systems' ability to fulfil the above criteria of oxidising teeth stains can be assayed by using the approach described below in the "Materials and Methods"-section.

According to the invention three types of oxidoreductases are specifically contemplated:

a) Laccases or related enzymes, which act on molecular oxygen and yield water ($H_2O$) without any need for peroxide (e.g. $H_2O$),
b) Oxidases, which acts on molecular oxygen ($O_2$) and yield peroxide ($H_2O_2$), and
c) Peroxidases, which act on peroxide (e.g. $H_2O_2$) and yield water ($H_2O$).

Also enzyme systems which comprise a combination of the three types of enzymes are contemplated according to the invention. The enzyme systems may e.g. consist of a laccase and an oxidase; a laccase and a peroxidase; a laccase and an oxidase and a peroxidase; or an oxidase and a peroxidase.

Preferred are the below mentioned enzymes, especially recombinant and/or substantially purified enzymes.

In the context of this invention "laccases and related enzymes" include enzymes comprised by the enzyme classification E.C. 1.10.3.2 (laccases) and catechol oxidase enzymes comprised by E.C. 1.10.3.1, bilirubin oxidase enzymes comprised by the enzyme classification E.C. 1.3.3.5 and mono-phenol mono-oxygenase enzymes comprised by the enzyme classification E.C. 1.14.99.1.

Preferably, the laccase employed is derived from a strain of Polyporus sp., in particular a strain of *Polyporus pinsitus* or *Polyporus versicolor*, or a strain of Myceliophthora sp., e.g. *M. thermophila* or a strain of Rhizoctonia sp., in particular a strain of *Rhizoctonia praticola* or *Rhizoctonia solani*, or a strain of a Rhus sp., in particular *Rhus vernicifera*.

In specific embodiments of the invention the oxidoreductase is a laccase, such as a Polyporus sp. laccase especially the *Polyporus pinisitus* laccase (also called *Trametes villosa* laccase) described in WO 96/00290 (from Novo Nordisk Biotec, inc.) or a Myceliophthora sp. laccase especially the *Myceliophthora thermophila* laccase described in WO 95/33836 (from Novo Nordisk Biotech inc).

Further, the laccase may be a Scytalidium sp. laccase, such as the *S. thermophilium* laccase described in WO 95/33837 (from Novo Nordisk Biotech inc.) or a Pyriculara sp. laccase, such as the *Pyriculara oryzae* laccase which can be purchased from SIGMA under the trade name SIGMA no. L5510, or a Copdnus sp. laccase, such as a *C. cinereus* laccase, especially a *C. cinereus* IFO 30116 laccase, or a Rhizoctonia sp. laccase, such as a *Rh. solani* laccase, especially the neutral *Rh. solani* laccase described WO 95/07988 (from Novo Nordisk A/S) having a pH optimum in the range from 6.0 to 8.5.

The laccase may also be derived from a fungi such as Collybia, Fomes, Lentinus, Pleurotus, Aspergillus, Neurospora, Podospora, Phlebia, e.g. *P. radiata* WO 92/01046), Coriolus sp., e.g. *C hirsitus* (JP 2-238885), or Botrytis.

Bilirubin oxidase may preferably be derived from a strain of Myrothecium sp., such as *M. verrucaria*.

Within the group of peroxidases classified under the Enzyme Classification number E.C. 1.11 (peroxidases) peroxidases (1.11.1.7) are especially contemplated.

The peroxidase of the invention may be derived from plants (e.g. horseradish peroxidase) or micro-organisms including fungi and bacteria such as a strain of Coprinus sp., such as *Coprinus cinereus* or *Coprinus macrorhizus*, or bacteria such as Bacillus, such as *Bacillus pumilus*.

In another embodiment of the invention the oxidoreductase is a peroxidase, such as a Coprinus sp. peroxidase, such as the *C. cinereus* peroxidase, such as *C. cinereus* IFO8371 or variants thereof described in WO 95/10602 (from Novo Nordisk A/S) being very stable in the presence of hydrogen peroxide, or a haloperoxidase originating from a strain of Curvularia sp. such as a *C. verrruculosa* haloperoxidase, in particular *C. verruculosa* CBS 147.63.

Oxidases which are contemplated include glucose oxidase (E.C. 1.1.3.4), hexose oxidase (E.C. 1.1.3.5), L-amino-acid oxidase (E.C. 1.4.3.2), xylitol oxidase, galactose oxidase (E.C. 1.1.3.9), pyranose oxidase (E.C. 1.1.3.10), alcohol oxidase (E.C. 1.1.3.13).

If a L-amino acid oxidase is used it may be derived from a Trichoderma sp. such as *Trichoderma hazianum*, such as the L-amino acid oxidase described in WO 94/25574 (from Novo Nordisk A/S), or *Trichoderma viride*.

A suitable glucose oxidase may originate from Aspergillus sp., such as a strain of *Aspergillus niger*, or from a strain of Cladosporium sp. in particular *Cladospofium oxysporum*, especially *Cl. oxysporum* CBS 163 described in WO 95/29996 (from Novo Nordisk A/S).

Hexose oxidases from the red sea-weed Chondrus crispus (commonly known as Irish moss)(Sullivan and Ikawa, (1973), Biochim. Biophys. Acts, 309, p. 11–22; Ikawa, (1982), Meth. in Enzymol. 89, carbohydrate metabolism part D, 145–149) oxidises a broad spectrum of carbohydrates, such as D-glucose, D-galactose, maltose, cellobiose, lactose, D-glucose 6-phasphate, D-mannose, 2-deoxy-D-glucole, 2-deoxy-D-galactose, D-fucase, D-glucurnic acid, and D-xylose.

Also the red sea-weed *Iridophycus flaccidum* produces easily extractable hexose oxidases, which oxidise several different mono- and disaccharides (Bean and Hassid, (1956), J. Biol. Chem, 218, p. 425; Rand et al. (1972, J. of Food Science 37, p. 698–710).

The broad substrate spectrum of hexose oxidase is advantageous in the connection with tooth bleaching as the total amount of usable substrate (i.e. carbohydrate) present in the mouth is significantly greater than for related enzymes having more specific catalytic properties.

Another relevant group of tooth bleaching enzymes is xylitol oxidases (see e.g. JP 80892242) which oxidises xylitol, D-sorbitol, D-galactitol, D-mannitol and D-arabinitol in into the presence of oxygen. A xylitol oxidase can be obtained from strains of Streptomyces sp. (e.g. Streptomyces IKD472, FERM P-14339) having a pH optimum at 7.5, is stable at pH 5.5 to 10.5 and at temperatures up to 65° C.; properties very well suited for oral care compositions and products. Further, the substrate xylitol is not cariogenic (i.e. is not degraded in the mouth to compounds responsible for dental holes).

It can be advantageous to use enzyme(s) which can act on substrates which are not cariogenic (i.e. substrates which are not or is not immediately degraded into cariogenic substrates such as sucrose, glucose, fructose, maltose etc.).

Examples of such a substrate include amino acids, alcohol, sugar alcohol, such as xylitol, sorbitol etc.

Consequently, in a preferred embodiment the oral care composition comprises one or more of the above enzymes and a substrate which is not cariogenic.

It is also advantageous to use enzymes being substantially active at pHs prevailing in the mouth, i.e. between pH 5.0 to 9.0, preferably between pH 6.0 to 8.5, especially between pH 6.4 to 7.5.

The term "substantially active" enzyme means in this context that the enzyme(s) has(have) an relative activity (pH-optimum defines 100% at the same conditions) higher than 30%, better 50%, even better more than 70%, such as 80%, and in the best case up to about 100% of the activity at the pH optimum.

In the case of using laccase and a peroxidase the bleaching effect can be obtained by direct oxidation of the teeth stains or via a mediator.

Oxidases generate peroxide ($H_2O_2$) in situ (i.e. in the oral cavity).

When using laccase and/or peroxidase, or an oxidase and a peroxidase no peroxide need to be present, while low concentrations of peroxide need to be added in the case of a peroxidase alone. However, it is also contemplated according to the invention to add low concentrations of peroxide when using laccase or oxidase.

It is to be understood that an advantage of the invention is that peroxide will not at any time be present in the oral cavity in concentrations which can inflict damage.

Compositions and products of the invention can be used safely without any major precautions by both the private consumer and professionals (i.e. dentists or the like) due to the low concentration or absence of hydrogen peroxide.

In a preferred embodiment the oral composition or oral care product of the invention comprises a redox mediator (sometimes called an enhancing agent or accelerator) which is an agent capable of enhancing the activity of oxidoreductases contemplated according to the invention.

The mediator may be any known mediator. Examples of such mediators are the following compounds: 2,2'-azino-bis (3-ethylbenzothiazoline-6-sulfonate (ABTS); 6-hydroxy-2-naphtoic acid; 7-methoxy-2-naphtol; 7-amino-2-naphthalene sulfonic acid; 5-amino-2-naphthalene sulfonic acid; 1,5-diaminonaphthalene; 7-hydroxy-1,2-naphthimidazole; 10-methylphenothiazine; 10-phenothiazine-propionic acid (PPT); N-hydroxysuccinimide-10-phenothiazine-propionate; benzidine; 3,3'-dimethylbenzidine; 3,3'-dimethoxybenzidine; 3,3',5,5'-tetramethylbenzidine; 4'-hydroxy-4-biphenylcarboxylic acid; 4-amino4'-methoxystilbene; 4,4'-diaminostilbene-2,2'-disulfonic acid; 4,4'-diaminodiphenylamine; 2,7-diaminofluorene; 4,4'-dihydroxy-biphenylene; triphenylamine; 10-ethyl-4-phenothiazinecarboxylic acid; 10-ethylphenothiazine; 10-propylphenothiazine; 10-isopropylphenothiazine; methyl-10-phenothiazinepropionate; 10-phenylphenothiazine; 10-allylphenothiazine; 10-phenoxazinepropionic acid (POP); 10-(3-(4-methyl-1-piperazinyl)propyl)phenothiazine; 10-(2-pyrrolidinoethyl)phenothiazine; 10-methylphenoxazine; iminostilbene; 2-(p-aminophenyl)-6-methylbenzothiazole-7-sulfonicacid; N-benzylidene-4-biphenylamine; 5-amino-2-naphthalenesulfonic acid; 7-methoxy-2-naphtol; 4,4'-dihydroxybenzophenone; N-(4-(dimethylamnino) benzylidene)-p-anisidine; 3-methyl-2-benzothiazolinone(4-(dimethylamino)benzylidene)hydrazone; 2-acethyl-10-methylphenothiazine; 10-(2-hydroxyethyl) phenothiazine;10-(2-hydroxyethyl)phenoxazine;10-(3-hydroxypropyl)phenothiazine; 4,4'-dimethoxy-N-methyl-diphenylamine; vanillin azine.

The amount of oxidoreductase(s) needed in an oral composition of the invention to obtain tooth bleaching depends on the particular compound employed, but ranges generally from 0.0001% to 20%, preferably from about 0.001% to about 10%, and most preferably from about 0.01% to about 5% by weight of the final composition.

In the preparation of an oral composition, the oxidoreductase(s) may for safety reasons be added as an essentially purified enzyme preparation. However, less purified oxidoreductases preparations can be used seen from a technical point of view.

The oral composition may be incorporated in products used for vital and/or non-vital tooth bleaching techniques. Examples of products suitable for vital tooth bleaching, having the main purpose of bleaching teeth, include products usually used by trained professionals in-office tooth bleaching and/or in the so-called "dental prescribed, home-applied"-products.

Especially contemplated according to the invention are "over-the-counter"-products, which include tooth bleaching kits and conventional oral care products.

Conventional oral care products are products, such as toothpastes, gels, mouth washes or denture cleaning agents usually primarily target dental caries, plaque and/or tartar. However, oral care products also targeting tooth stains (often called tooth whiteners) have been available on the consumer market for some years. However, these products use another bleaching/whitening principle.

The above mentioned types of products are described further in the above section "Background of the Invention".

The oral composition or oral care product of the invention may comprise at least one other enzyme activity, which includes the activity of a protease, and/or mutanase and/or dextranase and/or lipase and/or amylase and/or anti-microbial polypeptides or enzymes.

In a preferred embodiment of the invention the oral composition or oral care product comprise an oxidoreductase and a dextranase and/or a mutanase.

An oral composition of the invention may advantageously be used for in conventional oral care products having any suitable physical form (i.e. powder, paste, gel, liquid, ointment, tablet etc.).

In an embodiments the oral composition or oral care products are one-compartment products in air-free packages containing an oxidoreductase enzyme or enzyme system, especially a laccase, a redox mediator agent (e.g. ABTS or PPT) and further ingredients normally used in such oral compositions or oral care products.

In another embodiment the oral care compositions or oral care products are one-compartment products comprising an oxidase and the corresponding substrate with a limited amount of water or a none-aqueous dentifrice.

Even though the presence of a redox mediator is advantageous, as it improves the action of the tooth bleaching, it is not compulsory.

Also contemplated according to the invention are two-compartment oral compositions and oral care products, where the oxidoreductase (e.g. laccase) and the redox mediator are mixed immediately before introduction into the oral cavity.

An "oral care product" of the invention is defined as a product which can be used for maintaining and/or improving oral hygiene in the mouth of humans and animals, and/or preventing or treating dental diseases.

Examples of such oral care products include toothpaste, dental cream, gel or tooth powder, odontic, mouth washes, denture cleaning agents, pre- or post brushing rinse formulations, chewing gum, lozenges, and candy.

Toothpastes and tooth gels typically include abrasive polishing materials, foaming agents, flavouring agents, humectants, binders, thickeners, sweetening agents, and water.

Mouth washes, including plaque removing liquids, typically comprise a water/alcohol solution, flavour, humectant, sweetener, foaming agent, and colorant.

According to the invention said abrasive polishing material includes alumina and hydrates thereof, such as alpha alumina trihydrate, magnesium trisilicate, magnesium carbonate, sodium bicarbonate ("Baking soda"), kaolin, aluminosilicates, such as calcined aluminum silicate and aluminum silicate, calcium carbonate, zirconium silicate, and also powdered plastics, such as polyvinyl chloride, polyamides, polymethyl methacrylate, polystyrene, phenol-formaldehyde resins, melamine-formaldehyde resins, urea-formaldehyde resins, epoxy resins, powdered polyethylene, silica xerogels, hydrogels and aerogels and the like. Also suitable as abrasive agents are calcium pyrophosphate, water-insoluble alkali metaphosphates, dicalcium phosphate and/or its dihydrate, dicalcium orthophosphate, tricalcium phosphate, particulate hydroxyapatite and the like. It is also possible to employ mixtures of these substances.

Dependent on the oral care product the abrasive product may be present in from 0 to 70% by weight, preferably from 1% to 70%. For toothpastes the abrasive material content typically lies in the range from 10% to 70% by weight of the final toothpaste product.

Humectants are employed to prevent loss of water from e.g. toothpastes. Suitable in humectants for use in oral care products according to the invention include the following compounds and mixtures thereof: glycerol, polyol, sorbitol, polyethylene glycols (PEG), propylene glycol, 1,3-propanediol, 1,4butanediol, hydrogenated partially hydrolysed polysaccharides and the like. Humectants are in general present from 0% to 80%, preferably 5 to 70% by weight in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, can be mentioned as examples of suitable thickeners and binders, which help stabilizing the dentifrice product. Thickeners may be present in toothpaste creams and gels in an amount of from 0.1 to 20% by weight, and binders to the extent from 0.01 to 10% by weight of the final product.

As foaming agent soap, anionic, cationic, non-ionic, amphoteric and/or zwitterionic surfactants can be used. These may be present at levels from 0% to 15%, preferably from 0.1 to 13%, more preferably from 0.25 to 10% by weight of the final product.

Surfactants are only suitable to the extent that they do not exert an inactivation effect on the present enzymes. Surfactants include fatty alcohol sulphates, salts of sulphonated mono-glycerides or fatty acids having 10 to 20 carbon atoms, fatty acid-albumen condensation products, salts of fatty acids amides and taurines and/or salts of fatty acid esters of isethionic acid.

Suitable sweeteners include saccharin and/or other appropriate sweeteners.

Flavours, such as spearmint and peppermint, are usually present in low amounts, such as from 0.01% to about 5% by weight, especially from 0.1% to 5%.

Water is usually added in an amount giving e.g. toothpaste a flowable form, i.e. between 40% to 70% by weight of the final product.

Further water-soluble anti-bacterial agents, such as chlorhexidine digluconate, hexetidine, alexidine, quaternary ammonium anti-bacterial compounds and water-soluble sources of certain metal ions such as zinc, copper, silver and stannous (e.g. zinc, copper and stannous chloride, and silver nitrate) may also be included.

Also contemplated according to the invention is the addition of anticalculus agents, anti-plaque agents, compounds which can be used as fluoride source, dyes/colorants, preservatives, vitamins, pH-adjusting agents, antiaries agents, desensitizing agents etc.

A toothpaste produced from an oral composition of the invention (in weight % of the final toothpaste composition) may e.g. comprise the following ingredients:

| | |
|---|---|
| Abrasive material | 10 to 70% |
| Humectant | 0 to 80% |
| Thickener | 0.1 to 20% |
| Binder | 0.01 to 10% |
| Sweetener | 0.1% to 5% |
| Foaming agent | 0 to 15% |
| Bleaching enzyme | 0.0001% to 20% |
| Other enzymes | 0 to 20% |
| Peroxide | 0 to 1% |

Mouth washes

A mouth wash produced from an oral care composition of the invention (in weight % of the fanal mouth wash composition) may typically comprise the following ingredients:

| | |
|---|---|
| 0–20% | Humectant |
| 0–2% | Surfactant |
| 0–5% | Enzymes |
| 0–20% | Ethanol |
| 0–2% | Other ingredients (e.g. flavour, sweetener active ingredients such as florides). |
| 0–70% | Water |

The mouth wash composition may be buffered with an appropriate buffer e.g. sodium citrate or phosphate in the pH-range 67.5.

The mouth wash may be in none-diluted form (i.e. must be diluted before use).

Method of Manufacture

The oral care composition and products of the present invention can be made using methods which are common in the oral product area.

Finally the invention relates to a method for using an oral care product of the invention, wherein
 a) the oral care product is introduced into the mouth,
 b) contacted with the teeth and/or gums for a period of time,
 c) removed from the mouth, and
 d) optionally rinsed with a liquid.

If the oral care product to be used is in solid to flowable form a tooth brush or the like may advantageously be used for contacting the oral care product with the teeth and/or gums. In the case of a liquid oral care product the contact may take place by rinsing the mouth.

The time period of contact in step b) is optional. However, contacting the oral care product with the teeth and/or gums for between about 30 seconds to 15 minutes will normally be sufficient for obtaining the desired result.

After use, the oral care product may be removed from the mouth in any suitable way, e.g. by spitting it out. Optionally the mouth may be rinsed with a liquid, such as tap water.

METHODS AND MATERIALS

Materials:

Enzyme:

Laccase from *Myceliopthora thermophila,*(available from Novo Nordisk A/S).

Glucose oxidase from *Aspergillus niger* (available from Novo Nordisk A/S).

L-amino acid oxidase from *Trichoderma harzianum* (available from Novo Nordisk A/S).

Teeth:

Alike coloured teeth for the bleaching tests are selected by colour determination on the Minolta CR-221 Chroma Meter. The teeth are stored in water under refrigeration until use.

Solutions:
Staining broth A: (extrinsic stains)

| | |
|---|---|
| Clarified saliva* | 10 ml |
| Tea** | 10 ml |
| Coffee*** | 10 ml |
| Milk | 10 ml |

*Clarified saliva is prepared by the following steps:
chewing parafilm and collecting saliva,
centrifuging it and collecting the supernatant
**Pour 50 ml of boiled water on to one Lipton ™ Yellow label tea bag and leave it for 10 minutes.
***Regular coffee Staining broth B: (extrinsic stains)
100 ml autoclaved TSB (Tryptic Soy broth)
0.35 g instant coffee powder (Nescafen™, Classic)
0.25 g gastric mucin
Tea extract *
3.25 ml TSB broth with 24 hours aerobicly grown *Micrococcus luteus* DSM 20030T culture (from Nutrient agar plates grown for 2 days at 37° C.).
*40 ml boiling water is poured to tea from one bag of Lipton™ Yellow lable tea bag and are allowed to stand for 2 minutes. 15 ml of the supernatant is filtrated with a sterilized membrane, 0.45 $\mu$.
Straining broth C: (intrinsic stains)

| | |
|---|---|
| 2.5% BSA in 0.1 M phosphate buffer, pH 7. | 10 ml |
| 0.1 M Phosphate buffer, pH 7. | 2.5 ml |
| 0.2% chlorhexidine digluconate | 25 ml |
| 30% ribose | 12.5 ml |
| Incubate at 37° C. | |

Equipment:
Chroma Meter 210 (Minolta)
Methods:
Preparation of hydroxyapatite tablets
Hydroxyapatite tablets are prepared by compressing 250 mg of hydroxyapatite in a tablet die at about 5,900 kg (13,000 lbs) of pressure for 5 minutes. The tablets are then sintered at 600° C. for 4 hours and finally hydrated with sterile de-ionised water.
Sterilization of hydroxyanatite tablets
HA tablets are sterilised at 180° C. for two hours, hydrated with the sterilised de-ionised water and placed in a lid of Nunc tube (10 ml volume).
Stains of bovine teeth:
Bovine teeth are stained by immersing in staining broth A at 37° C. until teeth surface become brown.
HA tablets stained with pellicle
HA tablets are immersed in 2 ml of the staining broth B placed in a Nunc tube, rotated with approximately 30° angle for 5 seconds with an interval of 10 seconds at 37° C. The staining broth is replaced every 24 hours. The HA tablets are incubated for 3 days.
Assessment of the teeth colour
Quantitative teeth color assessment.
The color of teeth and hydroxyapatite tablets are measured before and after the enzyme treatment on a Chroma Meter 210. The Chroma Meter has a 3 mm diameter circular aperture for measuring optical properties of small areas. The meter provides values of the optical parameters L*, a* and b* in the CE system of colour measurement. $\Delta L^*$ is the difference of L* before and after a treatment which relates to the overall lightness or darkness change. Total colour difference is given by $\Delta E^*$ calculated with an equation below. A high positive value of $\Delta L^*$, indicating lightness.

$$\Delta E^* = \sqrt{\Delta L^{*2} = \Delta a^* + \Delta b^*}$$

The color of teeth should be measured after significant incubation of teeth in de-ionised water (at least 15 minutes at room temperature). The surface of teeth are wiped lightly with paper towel and the colour is measured.
L*: "0"=black and "100"=white
Determination of Laccase Activity (LACU)
Laccase activity is determined from the oxidation of syringaldazin under aerobic conditions. The violet colour produced is photometered at 530 nm. The analytical conditions are 19 $\mu$M syringaldazin, 23.2 mM acetate buffer, pH 5.5, 30° C., 1 minute reaction time.
1 laccase unit (LACU) is the amount of enzyme that catalyses the conversion of 1.0 $\mu$mole syringaldazin per minute under these conditions.
Determination of peroxidase activity units (POXU)
Peroxidase activity is measured in POXU/ml. (1 POXU (peroxidase unit) is defined as the amount of enzyme that catalyses the conversion of 1 $\mu$mole $H_2O_2$ per minute in a system where 2,2'-azinobis[3-ethylbenzothiazoline-6-sulfonate] is oxidised in the presence of 1 mM $H_2O_2$, pH 7.0, at a temperature of 40° C.)
Determination of glucose oxidase activity (GODU)
1 GODU is defined as the amount of enzyme which, under standard conditions, catalyses the formation of 1 micromole of $H_2O_2$ per minute. The analytic method AF266 is available upon request from Novo Nordisk A/S).

EXAMPLES

Example 1

Bleaching of extrinsic teeth stains with glucose oxidase (GOX)
Bovine teeth were immersed in staining broth A comprising tea, coffee, milk, and saliva at 37° C. until the teeth surface became brown as described in the Materials and Methods. section and treated with solution A and B, and Buffer as described below.

| | Solution A Enzyme | Solution B Glucose | Buffer |
|---|---|---|---|
| 1 | none | none (Buffer) | 50 mM Britton-Robinson pH 6.5 |
| 2 | Glucose oxidase 50 GODU/ml | 500 mM glucose | 50 mM Britton-Robinson pH 6.0 |

Both samples were prepared with Britton-Robinson buffer (pH 6.5)
Glucose solution was prepared one day before and kept at 4° C.
The glucose oxidase was derived from *Aspergillus niger*

Each solution was pre-incubated at 37° C. for 15 minutes prior to experiments
Two teeth were placed in a tube with 5.0 ml of solution A and 5.0 ml of solution B, respectively and incubation for 60 minutes at 37° C. A small magnetic stirrer was used for stirring the solutions. Both samples with buffer and oxidase+glucose, respectively, were treated this way. The treatment was repeated 3 times.
After incubation, the teeth were gently rinsed and the colour was measured as described in the Materials and Method section.

The result of the test is displayed in Table 1

TABLE 1

|  | ΔL* | ΔE* |
|---|---|---|
| Buffer | −0.15 | 3.13 |
| 25 GODU/ml glucose oxidase + 250 mM glucose | 0.74 | 1.80 |

As can be seen from the Table 1 glucose oxidase is capable of bleaching teeth with extrinsic stains.

Example 2
Bleaching of extrinsic stained hydroxy apatite tablets with L-amino acid oxidase Hydroxyapatite (HA) tablets were extrinsicly stained according to Stookey's method (Stookey G. K. et al. "In vitro Removal of Stains with Dentifrices", J. Dent. Res. 61, p. 1236 (1982)).

HA tablets (mimicking the properties of human enamel) sterilized as described in the Material and Methods section were immersed in staining broth B consisting of tea, coffee, mucin and *Micrococcus luteus* for 5 seconds with 10 seconds intervals at 37° C. as described above in the Materials and Method section. The HA tablets were incubated for 3 days. After staining the HA tablets were air dried and washed with de-ionised water Chromatographically pure L-amino acid oxidase from *Trichoderma hanianum* free from catalase activity was incubated with a L-Arginine solution prepared in 0.1 M sodium phosphate buffer pH 8.5.

Two stained HA tablets were treated with said L-amino acid oxidase solution by incubating in a total volume of 0.5 ml at 37° C. for 60 minutes with 90 reciprocal shaking/minutes.

The optical parameters L*, a* and b* were measured on a Chroma Meter as described in the Materials and Methods section.

The result of the test in displayed in Table 2

TABLE 2

|  | ΔL* | ΔE* |
|---|---|---|
| Buffer | −0.17 | 0.30 |
| 6 Units/ml L-amino acid oxidase + 100 mM L-Arginine | 1.04 | 1.07 |

As can be seen from the Table 2 L-amino acid oxidase is capable of bleaching teeth with extrinsic stains.

Example 3
Bleaching of extrinsic stained hydroxy apatite tablets with glucose oxidase Hydroxyapatite (HA) tablets were stained according to Stookey's method (Stookey G. K. et al. "In vitro Removal of Stains with Dentifrices", J. Dent. Res. 61, p. 1236 (1982)) and treated with chromatographically pure glucose oxidase from *Aspergillus niger*, free from catalase activity, incubated with a glucose solution prepared in 20 mM Britton-Robinson buffer, pH 6.0.

One stained HA tablet was treated with said glucose oxidase solution by incubating in a total volume of 10 ml at 39° C. for 60 minutes with 90 reciprocal shaking/minutes.

The optical parameters L*, a* and b* were measured on a Chroma Meter as described in the Materials and Methods section.

The result of the test in displayed in Table 3

TABLE 3

|  | ΔL* | ΔE* |
|---|---|---|
| Buffer | 2.18 | 2.97 |
| 500 mM glucose | 1.80 | 1.84 |
| 10 GODU/ml glucose oxidase + 100 mM glucose | 3.50 | 3.73 |
| 10 GODU/ml glucose oxidase + 500 mM glucose | 3.62 | 3.62 |
| 50 GODU/ml glucose oxidase + 500 mM glucose | 3.90 | 4.83 |
| 100 GODU/ml glucose oxidase + 500 mM glucose | 5.05 | 5.63 |

As can be seen from the Table 3 glucose oxidase is capable of bleaching teeth with extrinsic stains.

Example 4
Bleaching of extrinsic and intrinsic teeth stains with laccase

Bovine teeth were immersed in the staining broth (extrinsic stains) overnight at 37° C., transferred to staining broth c (intrinsic stains) and incubated at 37° C. until the tooth surface became brown.

|  | Solution A Enzyme | Solution B mediator |
|---|---|---|
| 1 | none (Buffer) | none (Buffer) |
| 2 | 0.6 LACU/ml Laccase | PTT 1000 μM |

Samples were all prepared with 50 mM Britton-Robinson buffer pH 6.5
The laccase was derived from *Myceliophthora thermophila*

Each of solutions A and B was pre-incubated at 37° C. for 15 minutes prior to experiments Two teeth were placed in a tube with 5.0 ml of solution A and 5.0 ml of solution B, respectively, and incubation for 60 minutes at 37° C. A small magnetic stirrer was used for stirring the samples. Both samples with buffer and Laccase +PPT, respectively, were treated this way. The treatment was repeated 3 times for each sample.

After incubation, the teeth were gently rinsed and the colour was measured as described in the Materials and Method section.

The result of the test is displayed in Table 4

TABLE 4

|  | ΔL* | ΔE* |
|---|---|---|
| Buffer | 0.01 | 1.53 |
| 0.3 LACU/ml laccase + 500 μM PPT | 2.67 | 2.78 |

As can be seen from the Table 4 laccase is capable of bleaching teeth with intrinsic stains. As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method for bleaching teeth, comprising contacting the teeth with an oral care product comprising an *Aspergillus niger* enzyme having glucose oxidese activity in an amount of from about 10 GODU/ml to about 100 GODU/ml under conditions and time suitable for bleaching teeth.

2. The method of claim 1, wherein the enzyme is substantially active between about pH 5.0 and about pH 9.0.

3. The method of claim 1, wherein the oral care product further comprises an enzyme selected from the group consisting of amylase, dextranase, lipase, mutanase, protease, and combinations of any of the foregoing.

4. The method of claim 1, wherein the oral care product further comprises glucose.

5. The method of claim 1, wherein the oral care product further comprises an anti-microbial activity.

6. The method of claim 1, wherein the oral care product is selected from the group consisting of a dentifrice, toothpaste, tooth powder, mouth wash, pro-rinse, and denture cleaning agent.

* * * * *